(12) United States Patent
Kemp

(10) Patent No.: US 7,908,092 B2
(45) Date of Patent: Mar. 15, 2011

(54) CHEMICAL SENSOR ARRAY EVALUATION METHOD

(75) Inventor: Thomas Kemp, Esslingen (DE)

(73) Assignee: Sony Deutschland GmbH, Cologne (DE)

( * ) Notice: Subject to any disclaimer, the term of this patent is extended or adjusted under 35 U.S.C. 154(b) by 1601 days.

(21) Appl. No.: 11/188,442

(22) Filed: Jul. 25, 2005

(65) Prior Publication Data

US 2006/0229820 A1  Oct. 12, 2006

(30) Foreign Application Priority Data

Jul. 26, 2004  (EP) .................................... 04017656

(51) Int. Cl.
*G06G 7/58* (2006.01)
*G01N 31/00* (2006.01)

(52) U.S. Cl. ........................................... 702/22; 703/12
(58) Field of Classification Search .................. None
See application file for complete search history.

(56) References Cited

U.S. PATENT DOCUMENTS

| 5,361,379 | A | * | 11/1994 | White | 382/227 |
| 2004/0098367 | A1 | | 5/2004 | Tamayo et al. | |
| 2005/0247114 | A1 | * | 11/2005 | Kahn et al. | 73/53.01 |

FOREIGN PATENT DOCUMENTS

WO  WO 02/09026  1/2002

OTHER PUBLICATIONS

Di Natale C et al: "Pattern recognition in gas sensing: Well-stated techniques and advances" Sensors and Actuators B, vol. 23, No. 2/3, Feb. 1995, pp. 111-118, XP004004799.

* cited by examiner

*Primary Examiner* — Marjorie Moran
*Assistant Examiner* — Anna Skibinsky
(74) *Attorney, Agent, or Firm* — Oblon, Spivak, McClelland, Maier & Neustadt, L.L.P.

(57) ABSTRACT

A method for identifying a chemical substance from a set of output states provided by a chemical sensor array being exposed to the chemical substance, the method including: selecting, with an evaluation circuit, from a set of class descriptions for different chemical substances a first class description and one or more further class descriptions, wherein the first class description is related to a first chemical substance and a further class description is related to a further chemical substance; and estimating, with one or more estimating units, a first likelihood value and one or more further likelihood values, wherein the first likelihood value represents a probability that the set of output states corresponds to the first class description, and a respective further likelihood value represents a probability that the set of output states corresponds to a respective further class description.

6 Claims, 3 Drawing Sheets

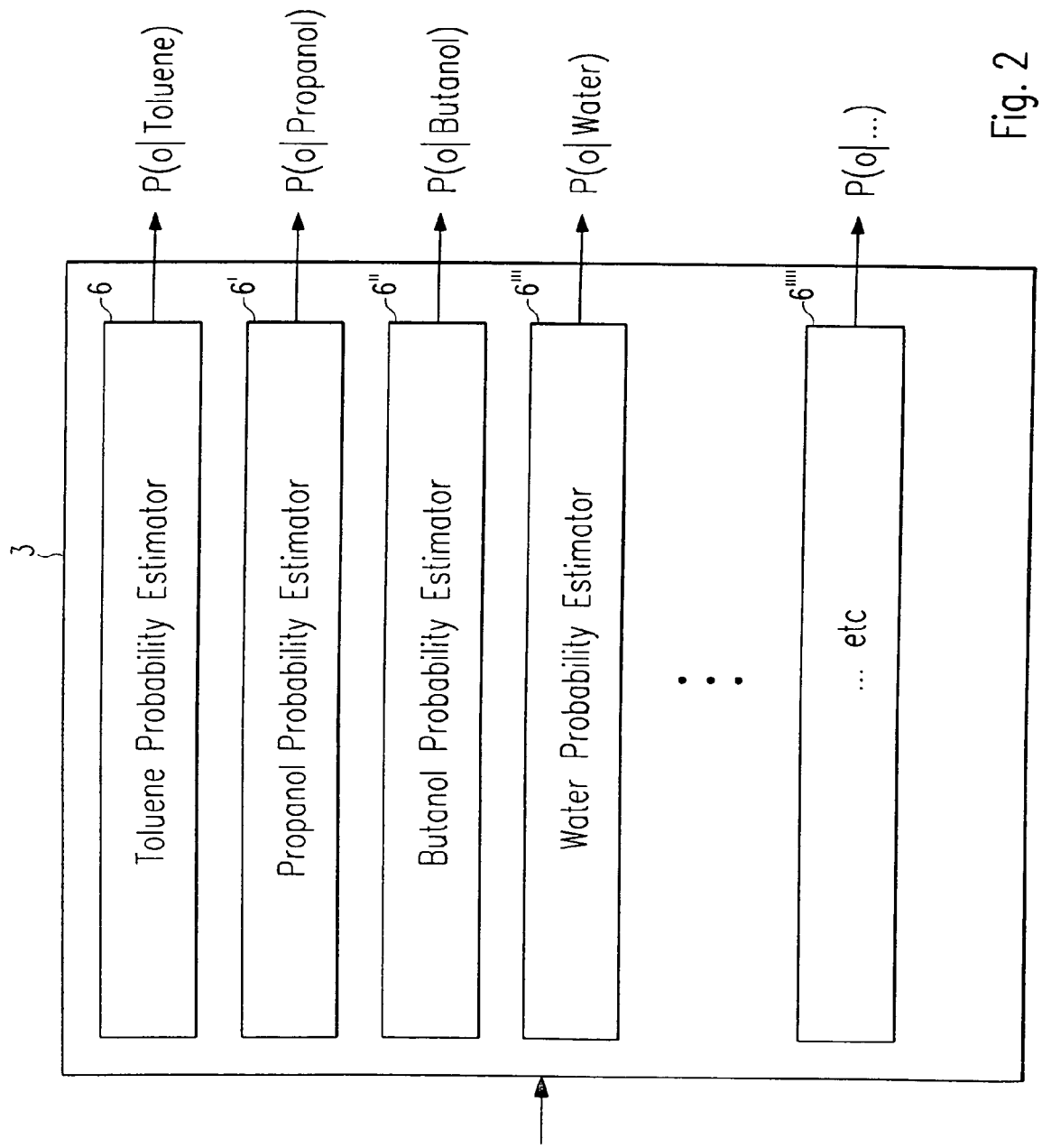

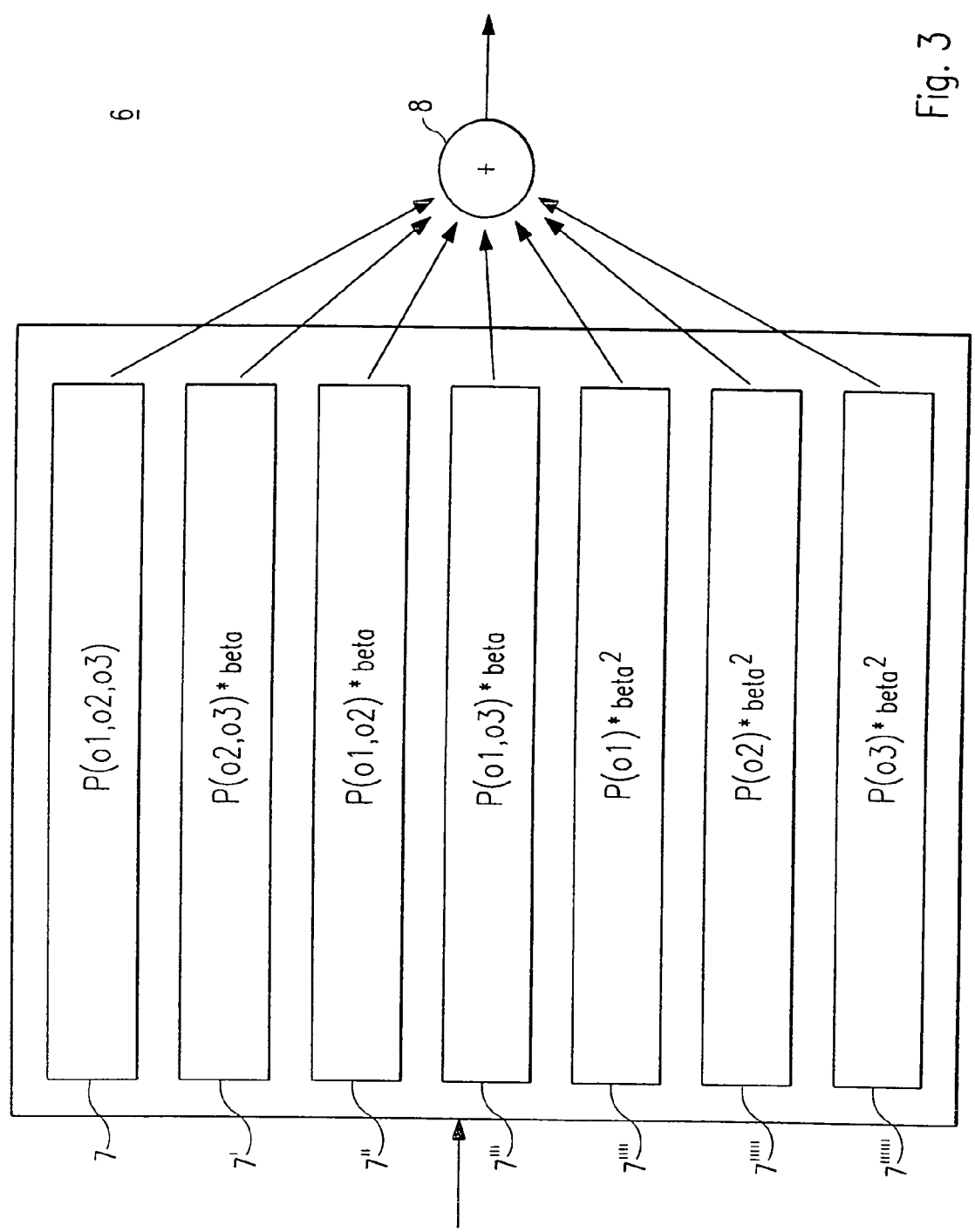

CHEMICAL SENSOR ARRAY EVALUATION METHOD

Figure 1:
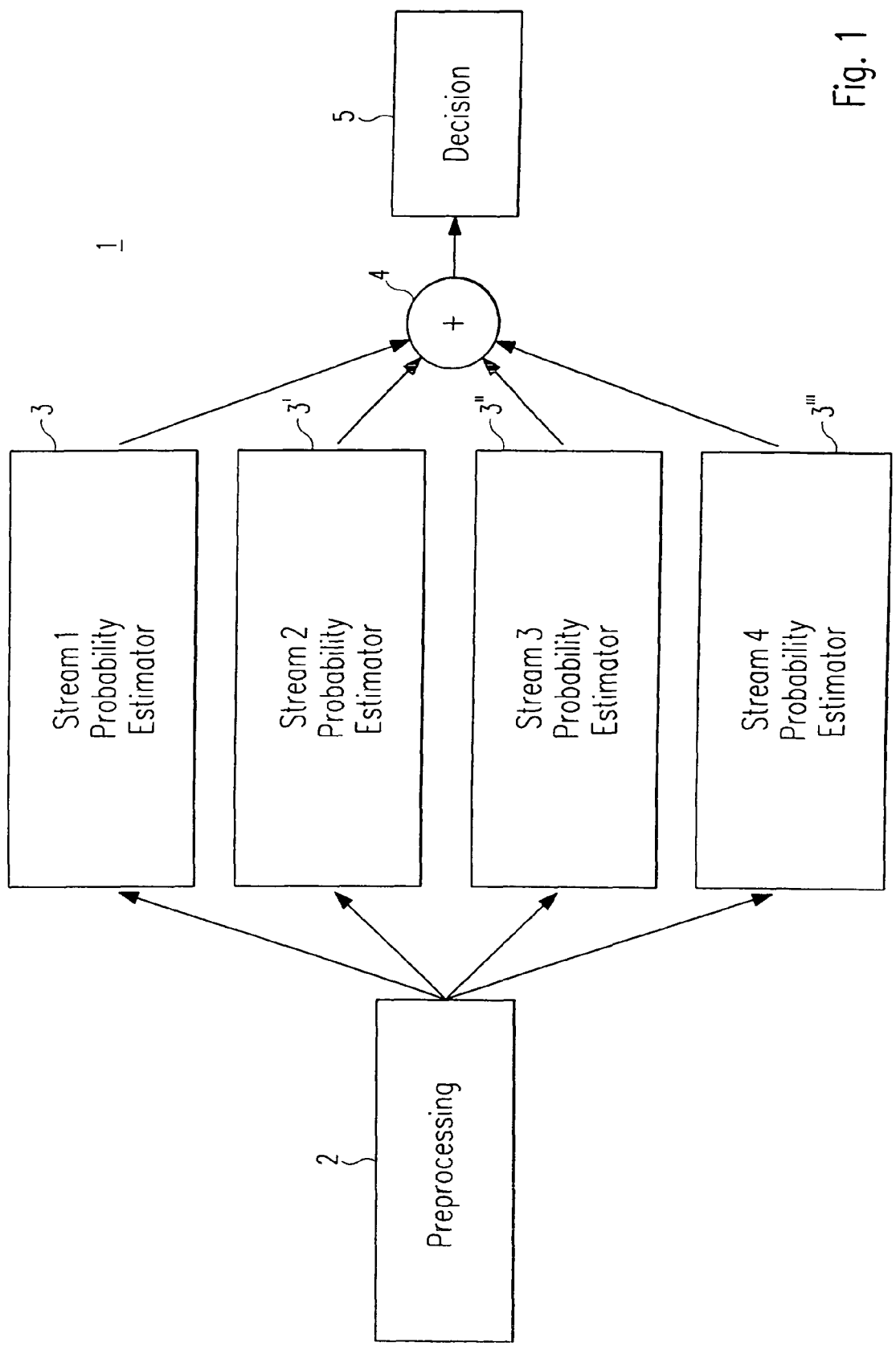

The present invention relates to an identification of chemical substances by use of chemical sensor arrays. It relates in particular to an evaluation circuit for identifying a chemical substance from a set of individual responses produced by sensors in the array exposed to the substance.

An array of chemical sensors combined with an evaluation circuit is typically referred to as an electronic nose. A chemical sensor is a device, which converts chemical information provided by a substance into an analytical signal. A respective sensor typically contains two functionally distinguishable components, a receptor and a transducer. The receptor part transforms the chemical information into a form of energy measured by the transducer, which generates the analytical signal. The analytical signal is available as a kind of output state of the sensor, e.g. in form of a voltage, current, capacity, inductivity, resistivity, frequency, pulse pattern or the like, which is supplied to an evaluation circuit for evaluating the chemical information contained in it.

Although the output state of a sensor reflects the presence of a certain chemical compound of a certain concentration at its receptor, the sensor is usually not selective enough for being sensitive to one distinct chemical compound only. Usually a chemical sensor shows a very broad selectivity, which means that it produces an analytical signal for more than just one distinct chemical compound. But the sensitivity of such a sensor, i.e. the relation between the value of the analytical signal produced in consequence of a compound being present at its receptor in a certain concentration, varies from substance to substance. The variation of a sensors sensitivity with respect to different chemical compounds is further different for different type of sensors.

For being able to tell an individual chemical compound apart from a given set of substances, several different chemical sensors can be combined to an array. The according improvement in selectivity is achieved by an utilization of the combined individual output states produced by the individual sensors of the array when exposed to the same analyte. While a single sensor produces just one output state of ambiguous chemical information, the combination of the individual output states to a set of analytical signals can provide an unambiguous substance identity information at least with respect to a given set of compounds used as analyte. For each chemical compound to which the sensor array is susceptible, the obtained set of analytical signals or set of output states, respectively, shows a characteristic pattern. By suitably normalising the set of output states, a pattern representation is achieved that is independent of the concentration of the analyte. This normalised pattern of output states is then evaluated by means of pattern recognition.

Simple pattern-recogniser compare a normalised pattern of output states obtained from the array with stored patterns for known compounds to determine the identity of the analyte. More sophisticated state of the art pattern recognition methods use normalised analytical signals obtained as a set of input readings '$i_1$' to '$i_N$' from the respective individual sensors number '1' to 'N' of the sensor array to determine the likelihood by which a certain set of input readings $[i_1, \ldots, i_N]$ can be classified as being representative for a certain chemical substance present at the receptors of the sensor array. The determination is implemented by a probability density function $p(i_1, \ldots, i_N | \text{class})$, which classifies the set of input readings $[i_1, \ldots, i_N]$ according to predefined class descriptions, whereby each class description represents just one instance from a set of chemical substances. By multiplying the probability density function with the a priori likelihood for the respective analyte p(class), the result is weighted according to previously ascertained expectations. In other words, the total probability that a set of input readings $[i_1, \ldots, i_N]$ obtained from the sensor array belongs to a certain substance is defined by the product of both probabilities. i.e. of $P(i_1, \ldots, i_N | \text{substance})$ and p(substance). The substance for which the product yields the highest value is then defined as the chemical substance representing the analyte. This can be expressed in a more formal way as in the following equation (1):

$$\text{Class} = \begin{pmatrix} \text{argmax} \\ \text{Class} \end{pmatrix} (p(i_1, \ldots, i_N | \text{class}) \cdot p(\text{class})) \quad (1)$$

A respective pattern recognition is only successful to a certain extent as most of the chemical sensors are subject to ageing. Ageing causes a degradation of a sensors performance and sometimes even failure. The resulting uncertainty in determining the correct substance can be overcome to a certain extent by combining sensors such, that the set of analytical signals provided by the array contains some redundancy. This means that the corresponding set of output states resembles an over-determined set of parameters for an evaluation of an analyte identity.

But unfortunately, the degradation of a sensor is usually a very individual process, so that the sensitivities of the various sensors in an array are not changing equally. Consequently, the pattern of a set of output states obtained for a distinct chemical compound or substance may change with time, thereby increasing the probability of a wrong analyte determination. Particularly when one sensor of the array fails, a common pattern-recogniser may from a certain time on no longer be able to identify an analyte correctly.

It is therefore an object of the present invention to provide an evaluation circuit for identifying a chemical substance based on a set of output states obtained from an array of chemical sensors exposed to the substance, whereby the identification is highly reliable also in case one or more of the sensors show a substantially degraded performance or even failure.

This object is achieved by the invention as defined in the independent claims.

According to an exemplary embodiment, there is a method for identifying a chemical substance from a set of output states provided by a chemical sensor array being exposed to the chemical substance is proposed, whereby the method includes: selecting from a set of class descriptions for different chemical substances a first class description and one or more further class descriptions, estimating a first likelihood value that represents a probability that the set of output states corresponds to the first class description and one or more further likelihood values that represent a probability that the set of output states corresponds to a respective further class description, and determining from the estimated first and further likelihood values the class description with the highest likelihood value. The first class description is hereby related to a first chemical substance and a further class description is related to a further chemical substance. In particular, an estimation of a first and further likelihood value combines the likelihood values estimated for at least two subsets of the set of output states corresponding to the first and further class description, respectively.

The above object is further achieved by a computer software product for identifying a chemical substance from a set of output states provided by a chemical sensor array being exposed to the chemical substance, the computer software product comprising a series of physically distinguishable states which are readable and executable by a processing unit, and which represent a sequence of instructions that perform a method according to the invention if executed by the processing means.

The above object is likewise achieved by an evaluation circuit for identifying a chemical substance from a set of output states provided by a chemical sensor array that is exposed to the chemical substance which comprises at least one probability estimation means for estimating a first and/or further likelihood value for a set or for a partial set of output states provided by the chemical sensor array, and a decision means for deciding which chemical substance corresponds to the set of output states or partial set of output states. The first likelihood value hereby represents a probability that the set of output states or the partial set of output states corresponds to a first class description of a set of class descriptions, and a respective further likelihood value represents a probability that the set of output states corresponds to a respective further class description of the set of class descriptions. The at least one probability estimation means is further adapted to determine a likelihood value for each class description of the set of class descriptions such, that the likelihood value for each class description is estimated in correspondence to a method according to the invention.

The present invention as defined in the independent claims allows a reliable identification of an analyte present at the receptors of a chemical sensor array even in case that not all sensors of the array are working properly, either due to malfunctioning or even failure. As no knowledge about the identity of a malfunctioning or failing sensor is necessary to keep up the performance, the maintenance requirements for an electronic nose using the present invention are minimised.

Advantageous embodiments of the present invention are the subject of sub-claims.

In a first embodiment a subset of the set of output states is formed by an output state of a single sensor of the chemical sensor array thus providing a valid value even if only one sensor of the array is left to operate normally. This is further supported by forming the sum of the likelihood values obtained for each of the thus defined subset of output states, since it enables a determination of a likelihood value until all sensors of the array are broken.

For a better accuracy, a subset of the set of output states is formed by a pair of output states with each output state of the pair originating from a different sensor of the chemical sensor array. Forming further the first and/or further likelihood value by the sum of the likelihood values obtained for each thus defined pair of output state subset, a likelihood value taking into account the correlation between the sensors of the array is achieved.

In a further preferred embodiment a first and/or further likelihood value is formed by the sum of a likelihood value obtained for a triplet of output states and a first weighted sum of likelihood values obtained for all possible pairs of output states contained in the triplet of output states, whereby each output state of the triplet originates from a different sensor of the chemical sensor array and a possible pair of output states is given by any two individual output states of the triplet of output states. This combines an improved accuracy of a likelihood determination based on the correlation between three sensors with a the robustness obtained for a sum of sub-classifiers, each of which is based on the correlation between only two sensors.

To further improve the robustness of the system, a second weighted sum of all likelihood values obtained for all individual output states of the triplet of output states is added to the first and/or further likelihood value. The weighting factor for the second weighted sum is hereby advantageously chosen smaller than the weighting factor for the first weighting sum and that both weighting factors are smaller one to put the emphasis on the accuracy of the likelihood estimation.

The probability estimation means and the decision means are preferably implemented in the evaluation circuit by means of a computer software product being executed by a processing means of the evaluation circuit.

In the following description, the present invention is explained in more detail with respect to special embodiments and in relation to the enclosed drawings, in which FIG. 1 shows the basic components of an evaluation circuit 1 according to the present invention for identifying a chemical substance from the readings of a chemical sensor array, FIG. 2 shows the components of a probability estimator according to the present invention, and FIG. 3 shows the components of an estimator sub-unit according to the present invention.

The present invention differs from what has been explained with respect to equation (1) by the way the total probability is evaluated for a set of input readings corresponding to a certain class description for a particular chemical substance. In equation (1) $p(i_1, \ldots, i_N|\text{class})$ models any correlation between the sensors of a respective chemical sensor array and therefore always requests a complete set of input readings $[i_1, \ldots, i_N]$. The present invention instead determines the likelihood by which an observation defined by a current set of input readings $[i_1, \ldots, i_N]$ corresponds to a certain class description based on a combination of probability contributions from subsets $[i_j, \ldots, i_k]$ of the input readings.

For a clear description of the invention, the details of it are described by way of example only for a chemical sensor array with only three sensors. But it is to be noted that the invention is not limited to a respective sensor array but is rather applicable to common chemical sensor arrays containing several tens of sensors and even more.

For a supposed array of three chemical sensors equation (1) reads:

$$\text{Class} = \begin{pmatrix} \text{argmax} \\ \text{Class} \end{pmatrix} (p(i_1, i_2, i_3 \mid \text{class}) \cdot p(\text{class})) \quad (1a)$$

$$= \begin{pmatrix} \text{argmax} \\ \text{Class} \end{pmatrix} (p(I \mid \text{class}) \cdot p(\text{class}))$$

The first probability expression $p(I|\text{class})$ in equation (1) resembles the total probability that a given observation $I=[i_1, i_2, i_3]$ corresponds to a class description 'class' that is representative for a particular chemical substance or compound, respectively. According to the invention, the probability expression $p(I|\text{class})$ is factorised in order to achieve a combination of likelihoods determined from subsets of the input readings forming the observation. In the most basic example, $p(I|\text{class})$ can be defined as the arithmetic average of all individual likelihood estimations, each of which is obtained based on an individual input reading $i_j$ only:

$$p(I|\text{class}) \sim p(i_1|\text{class}) + p(i_2|\text{class}) + p(i_3|\text{class}) \quad (2)$$

or in general terms:

$$p(I \mid \text{class}) \sim \sum_j p(i_j \mid \text{class}) \qquad (2a)$$

with $i_j \epsilon [i_1, \ldots, i_N]$.

The right sides of equations (2) and (2a) are of course not equivalent to the left sides, since the correlations between the individual sensors of the array are disregarded. In particular, the correlation between sensor number '1' and sensor number '2' as well as between sensor number '1' and sensor number three given by $p(i_1|i_2, i_3|\text{class})$, and the correlation between sensor number '2' and '3' given by $p(i_2, i_3|\text{class})$ have been dropped in these equations. This leads to a slight decrease in the accuracy of the resulting classifier $p(I|\text{class})$. Supposed, $i_j$ does not represent an individual sensor reading but a sub-selection of sensor readings $i_j=[i_u, \ldots, i_w]$ of an array with more than the described number of sensors, then the inaccuracy will also depend on the choice of the respective sub-selections.

The total probability given by the classifier $p(I|\text{class})$ is only reduced but not set to zero if one sensor of the array breaks. Assumed that one sensor, e.g. sensor number '2' of the exemplary array of three chemical sensors breaks or suffers from heavy degradation, then the reading of the respective sensor will be out of 'model space', i.e. the sensor will produce readings that are very different to its normal condition. Accordingly the sub-classifier associated to the sensor, e.g. $p(i_2|\text{class})$ will yield an extremely small value. But the remaining sub-classifiers are not affected from the sensor breakdown so that the total probability is only reduced by the contribution of the sub-classifier related to the broken sensor. The total probability that a current observation corresponds to the class description for Toluene may e.g. then look like in accordance to equation (2):

$$p(I|\text{Toluene})=0.27+0.000000002+0.13, \qquad (2b)$$

or in a formalised expression, since the contribution of $p(i_2|\text{Toluene})$ to the total probability can be ignored due to its tiny value:

$$p(I|\text{Toluene}) \sim p(i_1|\text{Toluene})+p(i_3|\text{Toluene}). \qquad (2c)$$

This means, that a broken sensor does no longer contribute to the overall probability. As a result of that, the overall probability for all class descriptions is on average reduced by about one third. But this will not affect the classification decision defined in equation (1), since all probabilities are scaled down equally. So, in net effect, a 'death' of sensor number '2' has only the effect that the probability calculation in equation (2) is implicitly reduced to "$p(i_1|\text{class})+p(i_3|\text{class})$", which would also be the mathematical form if the array would consist of only two sensors.

If two, or generally speaking all but one sensors of the array are broken, there is still one sub-classifier left to supply a likelihood value for each class description thus enabling a very reduced possibility but nevertheless at least a possibility for identifying an analyte. If e.g. only sensor number '1' is working properly, an estimation of the probability that a current observation corresponds to the class description for Toluene will be reduced to $p(i_1|\text{Toluene})$. A thus reduced probability estimation is of course not as reliable as one that is based on all input readings, but it is a lot better than getting no probability estimation at all.

In other words, the classifier defined by equation (2) is robust against the 'death' of any one or two sensors, and will continue to work as good as possible with the reduced subset. In practice $p(i_1|i_2)$ is not identical to $p(i_1)$, which means that the sensor readings $i_j$ are not independent from each other so that a slight decrease in classification accuracy will have to be taken into account.

The inaccuracy of a likelihood estimation according to equations (2) and (2a) can be overcome by combining sub-selections of input readings that contain the reading from more than one sensor. By defining the sub-selection as a pair of input readings originating from two sensors of the chemical sensor array, the total likelihood that a set of input readings belongs to a certain class description is then given by:

$$p(I|\text{class}) \sim p(i_1,i_2|\text{class})+p(i_1,i_3|\text{class})+p(i_2,i_3|\text{class}) \qquad (3)$$

for a three sensor array and in general terms by:

$$p(I \mid \text{class}) \sim \sum_{j,k} p(i_j, i_k \mid \text{class}) \qquad (3a)$$

with $i_j, i_k \epsilon [i_1, \ldots, i_N]$.

Like in the first example, the total probability is expressed as the arithmetic average of three sub-classifiers that stand completely on their own but which are based on different sensor subsets or input reading sub-selections, respectively. Each summand of equations (2) and (2a) like of equations (3) and (3a) therefore constitutes a valid example of a probability estimator for a class description.

A classifier according to equations (3) and (3a) takes possible correlations much better into account than a classifier according to equation (1), since in $p(i_j, i_k|\text{class})$ any correlation between a sensor number 'j' and a sensor number 'k' is modelled explicitly. If, in continuation of the above example, sensor number '2' 'dies' according to breakage, the first and the third term of equation (3) will yield very low likelihood values, and the sum will basically be made up by only the second term. However if two sensors 'die', a device defined by a three sensor array with a classifier according to equation (3) will be considered as broken. This is the main disadvantage of classifier (3) compared to classifier (2), while the disadvantage of classifier (2) with respect to classifier (3) can be seen in its lower accuracy performance due to the lack of modelling the correlation terms.

In a further embodiment of the invention, a classifier according to equations (3) and (3a), respectively, is combined with a classifier $p(i_1, i_2, i_3|\text{class})$ or $p(i_j, \ldots, i_k|\text{class})$, respectively, that models any correlation between the sensors of a respective array. For a three sensor array, such a kind of combination is defined by:

$$p(I \mid \text{class}) \sim p(i_1, i_2, i_3 \mid \text{class}) + \qquad (4)$$
$$\text{beta} \cdot p(i_1, i_2 \mid \text{class}) + p(i_1, i_3 \mid \text{class}) + p(i_2, i_3 \mid \text{class}))$$

wherein beta is a constant of a value smaller than one, for instance 0.1.

A general description of the combined classifier is given by:

$$p(I \mid \text{class}) \sim p(i_j, \ldots, i_k \mid \text{class}) + \text{beta} \cdot \sum_{j,k} p(i_j, i_k \mid \text{class}) \qquad (4a)$$

with $i_j, i_k \epsilon [i_1, \ldots, i_N]$.

If all sensors are working properly, the overall probability p(I|class) is dominated by the first term since beta is smaller than 1 and scales down the contributions of the second term. As the first term provides the most accurate modelling, equation (4) and (4a), respectively, provides the most accurate classifier. The second term of the equations (4) and (4a) provides the robustness of the classifier against a sensor breakage. If any one of the sensors in the array breaks, the first term will yield a value close to zero. Supposed sensor number '2' died' in a three sensor array, then the contributions from the first and third summand in the second term of equation (4) are nearly zero. The overall probability will then be reduced to $$p(I|class) \sim beta \cdot p(i_1, i_3|class). \tag{4b}$$

A classifier according to equation (4) or (4a), respectively, therefore provides the best possible performance if all sensors of a chemical sensor array work properly, and provides a still reliable performance in case any two sensors are operating within normal parameters. It is not necessary to know in advance or to detect explicitly which sensor might actually be broken. The systems works reliable regardless if all or only two sensors of the chemical sensor array operate properly.

But a classifier according to one of the equations (4) or (4a) will fail if all but one sensors break. This can be taken account of by defining the following classifier for a three sensor array:

$$p(I|class) \sim p(i_1, i_2, i_3|class) + \tag{5}$$
$$beta \cdot p(i_1, i_2|class) + p(i_1, i_3|class) + p(i_2, i_3|class)) +$$
$$beta^2 \cdot (p(i_1|class) + p(i_2|class) + p(i_3|class))$$

A general description of the classifier applying to sensor arrays of three and more chemical sensors is accordingly defined as:

$$p(I|class) \sim p(i_j, \ldots, i_k|class) + \tag{5a}$$
$$beta \cdot \sum_{j,k} p(i_j, i_k|class) + beta^2 \cdot \sum_j p(i_j|class)$$

with $i_j, i_k \in [i_1, \ldots, i_N]$.

For a chemical sensor array with more than three sensors, the scheme can easily be extended to include also correlations between more than two sensors. In practice this might not necessary improve the reliability of the sensor reading evaluation. Taking e.g. a chemical sensor array with four sensors, then the probability $p(i_1, i_2, i_3, i_4|class)$ could be in the same order of magnitude as the further term "$beta^3 \cdot p(i_3|class)$" even if the sensors number '1', '2', and '4' are all broken. The described case is very likely if 'beta' is very small so that 'beta$^3$' is nearly zero. Extending equation (5a) by introducing terms with further sensor correlations will thus improve the accuracy of the classifier for only one or a few sensors broken, but will leave it sensitive to a multiple sensor breakage. One may increase the value of beta, but this will put more weight on the secondary terms of the classifier, which do not consider the sensor correlation, so that the hereby achieved classifier robustness is bought at the price of a decreased quality for all sensors working properly.

For compensating a failure of any M sensors in a sensor array containing N sensors, a large number of combinations for sub-classifiers have to be taken into account, particularly for M≈N/2. This makes an implementation of a respective classifier extremely difficult since a determination of the total probability has to consider all possible failures in equal measure.

If a compensation is to be implemented for only one, but any one sensor of the array (M=1), a likelihood $P_{1,N}$ considering all possible sub-selections of correlated input readings is given by:

$$P_{1,N} = \sum_j p(i_1, \ldots, i_{r-1}, i_{r+1}, \ldots, i_N|class) \tag{6a}$$

with $r \in [1, \ldots, N]$.

Assumed N=5, then:

$$P_{1,5} = p(i_2, i_3, i_4, i_5|class) + p(i_1, i_3, i_4, i_5|class) + \tag{6}$$
$$p(i_1, i_2, i_4, i_5|class) + p(i_1, i_2, i_3, i_5|class) + p(i_1, i_2, i_3, i_4|class)$$

Each one of the five terms on the right side of equation (6) considers the failure of just one particular sensor. In the first term it is taken account of a failure of sensor number '1', in the second of sensor number '2' and so on. If it could be known in advance, which one of the sensors is going to fail, $P_1$ would be reduced to the corresponding term only.

If a failure of two sensors available in a sensor array is to be compensated for, a likelihood $P_{2,N}$ considering all possible sub-selections of correlated input readings is given by:

$$P_{2,N} = p(i_1, \ldots, i_{s-1}, i_{s+1}, \ldots, i_{t-1}, i_{t+1}, \ldots, i_N|class) \tag{7a}$$

with s, $t \in [1, \ldots, N]$ and $s \neq t$.

For a number of N=5 sensors in the sensor array, $P_2$ is composed of ten terms according to the scheme:

$$P_{2,5} = p(i_1, i_2, i_3|class) + p(i_1, i_2, i_4|class) + \tag{7}$$
$$p(i_1, i_2, i_5|class) + p(i_1, i_3, i_4|class) + p(i_1, i_3, i_5|class) +$$
$$p(i_1, i_4, i_5|class) + p(i_2, i_3, i_4|class) + \ldots$$

If a failure of M sensors available in an array of N sensors is to be compensated for, a likelihood $P_{M,N}$ considering all possible sub-selections of correlated input readings is composed of $$\binom{N}{M}$$

number of addends. This means that a great many of corresponding probability density functions has to be calculated, which is practically not feasible. To reduce the number of the probability functions to be calculated, each term of the likelihood $P_{M,N}$ can be approximated by a product of the individual likelihood estimations $p(i_j|class)$ corresponding to each sensor occurring in the respective term, according to the following example:

$$p(i_u, i_v, \ldots, i_z|class) \approx p(i_u|class) \cdot p(i_v|class) \cdot \ldots \cdot p(i_z|class) \tag{8}$$

with u, v, $\ldots$, $z \in [1, \ldots, N]$, and $u \neq v \neq \ldots \neq z$.

Although the expression on the right side of equation (8) differs somewhat from that on its left due to the disregard of the correlation between the individual sensors, it resembles a sufficient approximation. As each term in the likelihood expression $P_M$ is composed of the individual probability density functions of the single sensors, only these have to be calculated and only once. The individual addends of $P_M$ are then simply formed as a product of the respectively required individual probability density functions.

The total probability p(I|class) is then given by:

$$p(I|class)=p(i_1, i_2, \ldots, i_N|class)+beta \cdot P_{1,N}+ beta^2 \cdot P_{2,N}+ \ldots +beta^M P_{M,N}. \quad (9)$$

For a feasible handling, terms in equation (9) with an order higher than 2 are usually ignored, resulting in:

$$p(I|class) \approx p(i_1, i_2, \ldots, i_N|class)+beta \cdot P_{1,N}+beta^2 \cdot P_{2,N}. \quad (9a)$$

The basic elements of an evaluation circuit 1 for identifying a chemical substance from a set of individual responses produced by a chemical sensor array exposed to the substance are shown in FIG. 1. The evaluation circuit 1 contains a pre-processing unit 2, several probability estimators 3 to 3''', a combining unit 4, and a decision unit 5.

The pre-processing unit 2 treats the sensor responses in order to obtain input readings that are independent of a respective analyte concentration causing a current sensor response. All input readings together form a so called observation. The observation is supplied to several probability estimators 3 to 3''' (the number of probability estimators shown is just an example and not to be understood as limiting neither to using less or more), each of which processes a particular subset of the observation distinct to that of the others. The likelihood values resulting from each of the probability estimators 3 to 3''' are then combined by the combining unit 4 and the result of the combination is forwarded to the decision unit 5, which finally indicates the class description yielding the highest likelihood value for a current observation.

The construction of a probability estimator 3, which is identical to the others of FIG. 1 is shown in FIG. 2. It contains several probability estimator sub-units 6 to 6'''', each of which estimates the probability, that the sub-set of input readings received by the respective probability estimator 3 corresponds to a particular class description like e.g. a class description for Toluene, Propanol, Butanol, Water or the like.

Each of the probability estimator sub-units processes the different components of the total probability for the respective class description separately in different partial likelihood estimation units 7 to 7''''''. In the example shown, all partial probabilities necessary for a classifier according to equation (5) are evaluated and correspondingly combined.

All components and sub-components of an evaluation circuit described with reference to the attached Figures are preferably implemented by a computer software product that is executed by a processing means of the evaluation circuit.

The present invention enables the construction of an electronic nose, i.e. a chemical sensor array with a pattern recognition evaluation circuit that is robust against failure of one or more of the chemical sensors in the array. It will still perform nearly as if it had been designed without the broken sensor right from the beginning. It is thereby not necessary to detect which sensor failed, and no modification inside the electronic nose is necessary to compensate for the sensor failure. If a sensor's 'death' is only temporary, e.g. by poisoning it with some inappropriate substance, the electronic nose will automatically return to full performance as soon as the respective sensor works within parameters and without a need to validate the return of the sensor. Thus, an electronic nose with a sensor reading processing according to the present invention provides a significantly improvement robustness with respect to sensor failing.

The invention claimed is:

1. A method for identifying a chemical substance from a set of output states provided by a chemical sensor array being exposed to the chemical substance, the method comprising:
   selecting, with an evaluation circuit, from a set of class descriptions for different chemical substances a first class description and one or more further class descriptions, wherein the first class description is related to a first chemical substance and a further class description is related to a further chemical substance;
   estimating, with one or more estimating units, a first likelihood value and one or more further likelihood values, wherein the first likelihood value represents a probability that the set of output states corresponds to the first class description, and a respective further likelihood value represents a probability that the set of output states corresponds to a respective further class description; and
   determining, with a processing means, from the estimated first and further likelihood values the class description with a highest likelihood value,
   wherein the estimating of the first likelihood value and one or more further likelihood values includes combining likelihood values estimated for at least two subsets of the set of output states corresponding to the first and further class description, respectively,
   said set of output states contains an over-determined set of output states, and
   at least one of the first likelihood value or the further likelihood values is formed by a sum of a likelihood value obtained for a triplet of output states with a first weighted sum of likelihood values obtained for all possible pairs of output states contained in the triplet of output states, each of said pairs constituting a subset, and each output state of the triplet of output states originates from a different sensor of the chemical sensor array and a possible pair of output states is given by any two individual output states of the triplet of output states.

2. The method according to claim 1, wherein a further subset of the set of output states is formed by an output state of a single sensor of the chemical sensor array.

3. The method according to claim 2, wherein at least one of the first likelihood value or the further likelihood values is formed by a sum of likelihood values obtained for each subset of output states.

4. The method according to claim 1, wherein a second weighted sum of all likelihood values obtained for all individual output states of the triplet of output states is added to at least one of the first likelihood value or the further likelihood values.

5. The method according to claim 4, wherein a weighting factor for the second weighted sum is smaller than a weighting factor for the first weighting sum and that both weighting factors are smaller than one.

6. An evaluation circuit for identifying a chemical substance from a set of output states provided by a chemical sensor array being exposed to the chemical substance, the evaluation circuit comprising:
   processing means for executing software;
   selecting means for selecting from a set of class descriptions for different chemical substances a first class description and one or more further class descriptions, wherein the first class description is related to a first chemical substance and a further class description is related to a further chemical substance;
   at least one probability estimation means for estimating a first likelihood value and a further likelihood value for a set or for a partial set of output states provided by the chemical sensor array, wherein the first likelihood value represents a probability that the set of output states or the partial set of output states corresponds to the first class description of a set of class descriptions, and a respective further likelihood value represents a probability that the set of output states corresponds to a respective further class description of the set of class descriptions; and a decision means for deciding which chemical substance corresponds to the set of output states or partial set of output states, wherein the at least one probability estimation means estimates the first likelihood value and the further likelihood value by combining likelihood values estimated for at least two subsets of the set of output states corresponding to the first and further class description, respectively, said subset of output states contains an over-determined set of output states, and at least one of the first likelihood value or the further likelihood values is formed by a sum of a likelihood value obtained for a triplet of output states with a first weighted sum of likelihood values obtained for all possible pairs of output states contained in the triplet of output states, each of said pairs constituting a subset, and each output state of the triplet of output states originates from a different sensor of the chemical sensor array and a possible pair of output states is given by any two individual output states of the triplet of output states.

* * * * *